(12) United States Patent
Ghanem et al.

(10) Patent No.: US 9,751,985 B2
(45) Date of Patent: Sep. 5, 2017

(54) TRIPTYCENE-BASED DIANHYDRIDES, POLYIMIDES, METHODS OF MAKING EACH, AND METHODS OF USE

(71) Applicant: King Abdullah University of Science and Technology, Thuwal (SA)

(72) Inventors: Bader Ghanem, Thuwal (SA); Ingo Pinnau, Thuwal (SA); Raja Swaidan, Thuwal (SA)

(73) Assignee: King Abdullah University of Science and Technology, Thuwal (SA)

( * ) Notice: Subject to any disclaimer, the term of this patent is extended or adjusted under 35 U.S.C. 154(b) by 0 days.

(21) Appl. No.: 14/894,617

(22) PCT Filed: Jun. 9, 2014

(86) PCT No.: PCT/IB2014/001721
§ 371 (c)(1),
(2) Date: Nov. 30, 2015

(87) PCT Pub. No.: WO2014/207559
PCT Pub. Date: Dec. 31, 2014

(65) Prior Publication Data
US 2016/0102177 A1    Apr. 14, 2016

Related U.S. Application Data

(60) Provisional application No. 61/831,684, filed on Jun. 6, 2013.

(51) Int. Cl.
*B01D 53/22* (2006.01)
*B01D 71/64* (2006.01)
*C08G 73/10* (2006.01)
*C07D 493/22* (2006.01)

(52) U.S. Cl.
CPC ....... *C08G 73/1085* (2013.01); *B01D 53/228* (2013.01); *B01D 71/64* (2013.01); *C07D 493/22* (2013.01); *C08G 73/1053* (2013.01); *C08G 73/1075* (2013.01); *C08G 73/1078* (2013.01)

(58) Field of Classification Search
CPC ...... B01D 53/228; B01D 71/62; B01D 71/64; C08G 73/1053; C08G 73/1075; C08G 73/1078; C08G 73/1082; C08G 73/1085
See application file for complete search history.

(56) References Cited

U.S. PATENT DOCUMENTS

| | | | |
|---|---|---|---|
| 5,262,056 A | 11/1993 | Koros et al. | |
| 6,649,283 B1 * | 11/2003 | Lupo | H01L 51/0035 313/502 |
| 2002/0150697 A1 * | 10/2002 | Swager | C08G 61/02 428/1.1 |
| 2006/0246273 A1 * | 11/2006 | McKeown | B01D 53/228 428/314.8 |
| 2010/0151154 A1 | 6/2010 | Hirai | |
| 2013/0267616 A1 * | 10/2013 | McKeown | C08G 73/0694 521/27 |

FOREIGN PATENT DOCUMENTS

| | | |
|---|---|---|
| CN | 1674293 A | 9/2005 |
| CN | 101481378 A | 7/2009 |
| JP | 2004-182962 | 7/2004 |
| JP | 2004-359599 | 12/2004 |

OTHER PUBLICATIONS

Hou, Xiao-wei et al., "Synthesis of New Polyimides Containing Triptycene", Journal of Huaqiao University (Natural Science), Sep. 2011, vol. 32, No. 5, pp. 532-536.*
Ghanem, Bader, "A facile synthesis of novel triptycene-containing A-B monomer: precursor to polymers of intrinsic microporosity", Polymer Chemistry, 2012, 3, pp. 96-98. Published on Oct. 26, 2011.*
Zhang, Quanyuan et al., "Synthesis and properties of novel organosoluble polyimides derived from 1,4-bis[4-(3,4-dicarboxylphenoxy)]triptycene dianhydride and various aromatic diamines", 2007, Polymer, 48, pp. 6246-6253.*
Chinese Office Action Application No. 201480032511.X dated Jul. 28, 2016, 5 pages.
Hou, Xiao-wei, et al. "Synthesis of New Polyimides Containing Triptycene." Journal of Huaqiao University (Natural Science) 5 (2011): 014. (with English abstract).
Ghanem, Bader S. "A facile synthesis of a novel triptycene-containing A—B monomer: precursor to polymers of intrinsic microporosity." Polymer Chemistry 3.1 (2012): 96-98.
International Search Report and Written Opinion of Application No. PCT/IB2014/001721 dated Mar. 17, 2015 10 pages.

\* cited by examiner

*Primary Examiner* — Jason M Greene
(74) *Attorney, Agent, or Firm* — Thomas | Horstemeyer, LLP

(57) ABSTRACT

A triptycene-based monomer, a method of making a triptycene-based monomer, a triptycene-based aromatic polyimide, a method of making a triptycene-based aromatic polyimide, methods of using triptycene-based aromatic polyimides, structures incorporating triptycene-based aromatic polyimides, and methods of gas separation are provided. Embodiments of the triptycene-based monomers and triptycene-based aromatic polyimides have high permeabilities and excellent selectivities. Embodiments of the triptycene-based aromatic polyimides have one or more of the following characteristics: intrinsic microporosity, good thermal stability, and enhanced solubility. In an exemplary embodiment, the triptycene-based aromatic polyimides are microporous and have a high BET surface area. In an exemplary embodiment, the triptycene-based aromatic polyimides can be used to form a gas separation membrane.

26 Claims, No Drawings

TRIPTYCENE-BASED DIANHYDRIDES, POLYIMIDES, METHODS OF MAKING EACH, AND METHODS OF USE

CROSS-REFERENCE TO RELATED APPLICATIONS

This application is the National Stage of International Application No. PCT/IB2014/001721, filed 9 Jun. 2014, which claims the benefit of and priority to U.S. Provisional Application No. 61/831,684, filed on 6 Jun. 2013, having the title "TRIPTYCENE-BASED DIANHYDRIDES, POLYIMIDES, METHODS OF MAKING EACH, AND METHODS OF USE", the contents of all of which are incorporated by reference as if fully set forth herein.

BACKGROUND

Gas separation is an emerging technology with a rapidly developing market comprising applications like air separation for oxygen or nitrogen enrichment as well as acid gas removal and hydrocarbon recovery from natural gas streams. The economics of a membrane-based separation system depend on the gas permeability (thickness- and pressure-normalized flux) and selectivity (preferential permeation of one gas over another) of the material used. Unfortunately, there is a conventional trade-off between these two main parameters such that an increase in permeability is concurrent with a decrease in selectivity, and vice versa. This results in what is commonly referred to as an "upper-bound" to performance which is defined by polymeric materials with the highest known combinations of permeability and selectivity. It is revised to accommodate discoveries of better performing polymers and is therefore taken as a gauge of the state-of-the-art.

Polyimides are one dominant class of polymers developed by major competitors in the membrane-based gas separation industry for a range of gas separation applications including air separations (oxygen/nitrogen enrichment) and hydrogen separations (hydrogen recovery from ammonia purge-gas streams) as well as the removal of acid gases ($CO_2$ and $H_2S$) and higher hydrocarbons ($C_2+$) from natural gas. Polyimides, typically formed by the polycondensation reaction between a diamine and dianhydride followed by the cyclodehydration step, have a versatile structure amenable to simple, systematic changes. They are well known as high performance polymers which possess high thermal and chemical stabilities, good mechanical and superior film-forming properties. However, current polyimides do not address current gas separation needs, and therefore, new polyimides are desirable.

Discussion

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, polymer chemistry, analytical chemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in bar. Standard temperature and pressure are defined as 0° C. and 1 bar.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions:

The term "substituted" refers to any one or more hydrogens on the designated atom that can be replaced with a selection from the indicated group, provided that the designated atom's normal valence is not exceeded, and that the substitution results in a stable compound.

As used herein, "alkyl" or "alkyl group" refers to a branched saturated aliphatic hydrocarbon. Examples of alkyl include, but are not limited to iso-propyl, sec-butyl, t-butyl, and iso-pentyl.

The term "substituted," as in "substituted alkyl", "substituted aryl," "substituted heteroaryl" and the like means that the substituted group may contain in place of one or more hydrogens a group such as alkyl, hydroxy, amino, halo, trifluoromethyl, cyano, —NH(lower alkyl), —N(lower alkyl)$_2$, lower alkoxy, lower alkylthio, or carboxy, and thus embraces the terms haloalkyl, alkoxy, fluorobenzyl, and the sulfur and phosphorous containing substitutions referred to below.

As used herein, "halo", "halogen", or "halogen radical" refers to a fluorine, chlorine, bromine, and iodine, and radicals thereof. Further, when used in compound words, such as "haloalkyl" or "haloalkenyl", "halo" refers to an alkyl or alkenyl radical in which one or more hydrogens are substituted by halogen radicals. Examples of haloalkyl include, but are not limited to, trifluoromethyl, trichloromethyl, pentafluoroethyl, and pentachloroethyl.

The term "aryl" as used herein, refers to an aromatic monocyclic or multicyclic ring system of about 6 to about 14 carbon atoms, preferably of about 6 to about 10 carbon atoms. Exemplary aryl groups include phenyl or naphthyl, or phenyl substituted or naphthyl substituted.

The term "heteroaryl" is used herein to denote an aromatic ring or fused ring structure of carbon atoms with one or more non-carbon atoms, such as oxygen, nitrogen, and sulfur, in the ring or in one or more of the rings in fused ring structures. Preferred examples are furanyl, imidazyl, pyranyl, pyrrolyl, and pyridyl.

General Discussion

Embodiments of the present disclosure provide for a triptycene-based monomer, a method of making a triptycene-based monomer, a triptycene-based aromatic polyimide, a method of making a triptycene-based aromatic polyimide, methods of using triptycene-based aromatic polyimides, structures incorporating triptycene-based aromatic polyimides, methods of gas separation, and the like. Embodiments of the triptycene-based aromatic polyimides have one or more of the following characteristics: intrinsic microporosity, good thermal stability, and enhanced solubility. Intrinsic microporosity is defined herein as a polymeric material with pore sizes of less than 2 nm and a surface porosity of >100 m$^2$/g, as determined by nitrogen adsorption method at 77 K. Attachment A includes exemplary reactions schemes and gas separation data for an embodiment of a triptycene-based aromatic polyimide.

Embodiments of the triptycene-based monomers and triptycene-based aromatic polyimides are expected to be economically attractive compared with the current polymer-based membranes due to their high permeabilities and excellent selectivities. Higher permeability offers savings in capital cost of membrane systems by reducing area requirements to handle a given process flow. It also reduces energy consumption by reducing compression requirements. Higher selectivity introduces large savings by reducing crossover of valuable gas feed components into the permeate streams and also by reducing the need for multi-stage systems.

In an exemplary embodiment, a triptycene-based aromatic polyimide can be used to form a gas separation membrane. The membrane can have exceptional performance for gas separation applications significantly transcending the upper bounds. Specifically, embodiments of membranes incorporating the triptycene-based polyimide provide unprecedented performance in gas separation applications including nitrogen enrichment and hydrogen recovery from ammonia purge-gas streams. In addition, embodiments of membranes incorporating the triptycene-based polyimide have excellent performance in olefin/paraffin ($C_3H6$ $C_3H8$) and natural gas sweetening ($CO_2$/CH) applications.

In an exemplary embodiment, triptycene-based aromatic polyimides are microporous and have the highest BET surface area (e.g., up to 850 m$^2$/g) of all previously reported non-network polyimides, as conventionally measured by the area accessible to $N_2$ molecules at 77K. The microporosity and the good solubility (processability) of these materials appears to have resulted from the incorporation of the rigid three-dimensional structure of a triptycene moiety, which prevents the close packing of the polymer chains and decreases the interchain interactions. Embodiments of these polyimides demonstrate performance significantly transcending the upper-bounds for important gas separation applications. In particular, exemplary embodiments of the triptycene-based aromatic polyimides when used in gas separation membranes demonstrate unprecedented combinations of permeability and selectivity in air separations (i.e., $O_2/N_2$ in nitrogen enrichment), hydrogen separations (i.e., $H_2/N_2$ and $H_2/CH_4$ for hydrogen recovery from ammonia purge gas streams), and challenging olefin/paraffin separations (i.e., C3H6/C3H8). Furthermore, these materials show excellent performance relative to the upper-bound for $CO_2/CH_4$ separations (natural gas sweetening). Attachment A includes data that describes the gas separation properties of membranes made from the triptycene-based aromatic polyimide of the present disclosure.

In addition, due to their good solubilities, thermal and chemical stabilities, and high microporosities, these materials can be implemented in a wide range of industrial applications related to thermally stable coatings, low dielectric constant films, optoelectronic materials, sensors, and gas storage media.

In an exemplary embodiment, the triptycene-based aromatic polyimide can be made using a triptycene-based monomer as shown in the following structure:

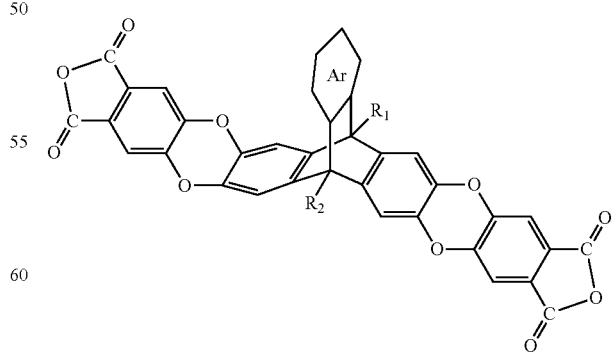

In an embodiment, AR can be a substituted or un-substituted aromatic moiety. In an exemplary embodiment, the substituted or un-substituted aromatic moiety can be: a substituted or un-substituted aryl group, a substituted or un-substituted heteroaryl group. In an embodiment, AR can be one of the groups shown in Scheme 2.

In an embodiment, R1 and R2 can each independently be hydrogen or a substituted or non-substituted alkyl group. In particular, R1 and R2 can each be independently substituted or un-substituted branched C3 to C5 alkyl groups.

Representative triptycene-based monomers can have the following structures:

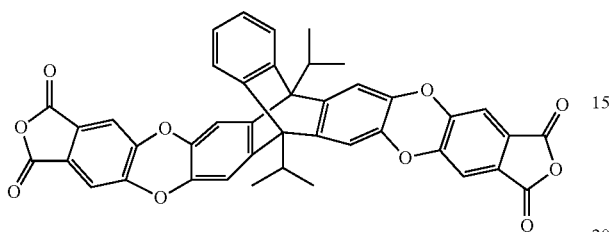

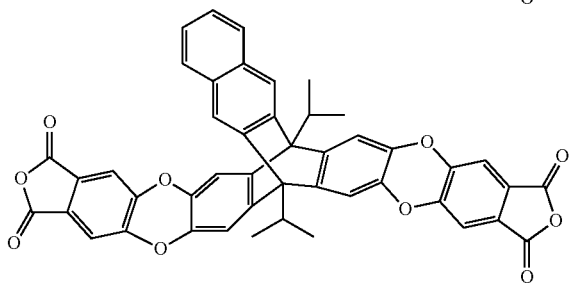

In an exemplary embodiment, the triptycene-based monomer can be synthesized using the synthesis described in Scheme 1 in Attachment A. Although some specific solvents, acids, and other reagents are described, other suitable solvent, acids, and reagents can be used if they accomplish the same purpose. R can include the same groups as R1 and R2.

In an exemplary embodiment, the triptycene-based aromatic polyimide can include a compound as represented by the following structure:

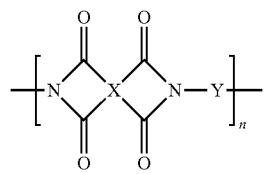

In an embodiment, n can be 1 to 10,000. In an exemplary embodiment, X can be a triptycene-based monomer as describe above. In an exemplary embodiment, Y can be a divalent organic group. In an embodiment, Y can be represented by AR', where AR' can be a group as described in Scheme 2, Attachment A. AR' corresponds to the base of various diamines that can be used to form the polyimide. In an embodiment, the divalent organic group is selected from the group consisting of: a substituted or un-substituted aryl group, a substituted or un-substituted heteroaryl group.

Representative triptycene-based aromatic polyimides can have the following structures:

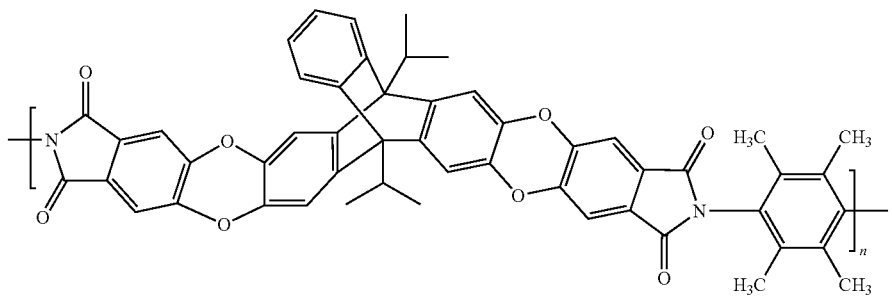

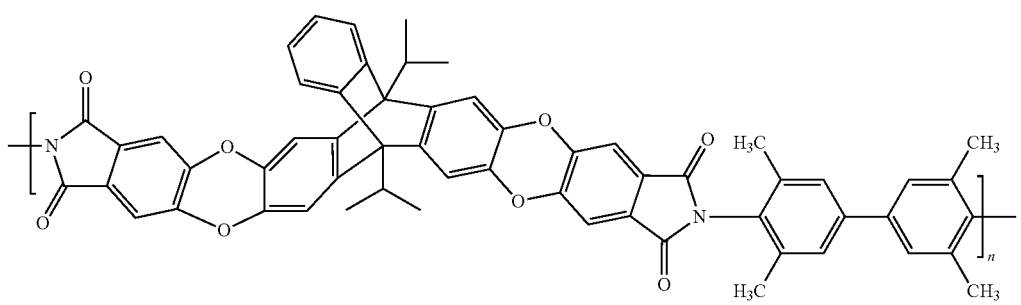

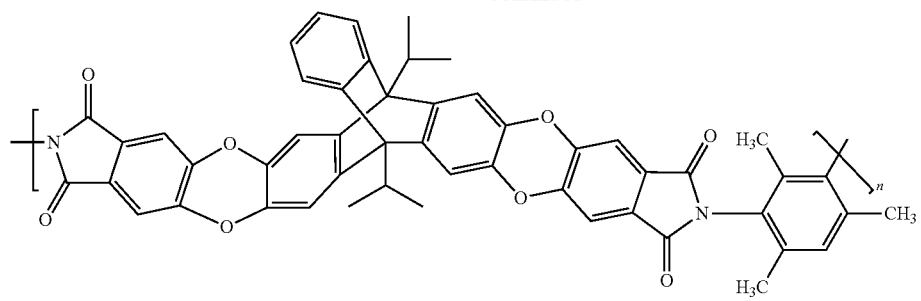
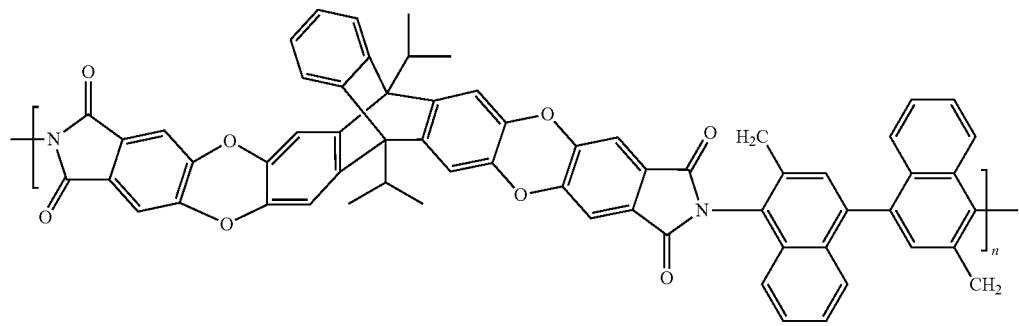
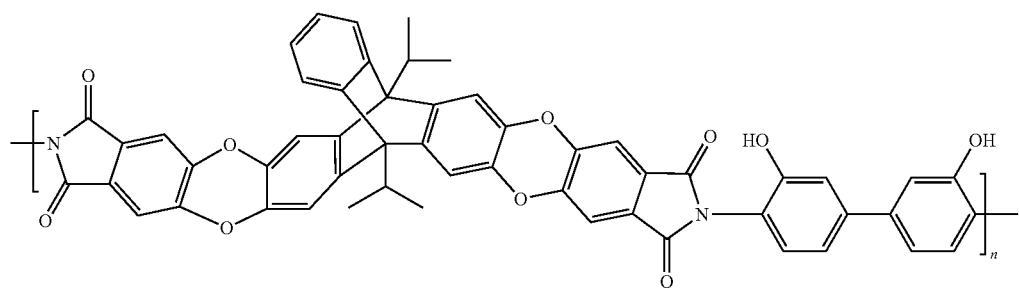
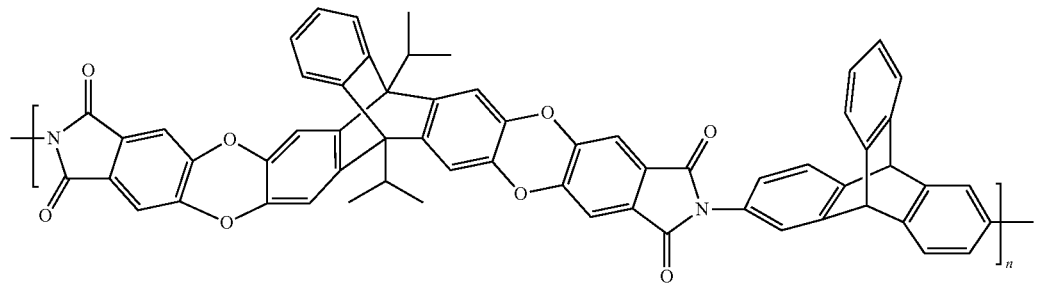
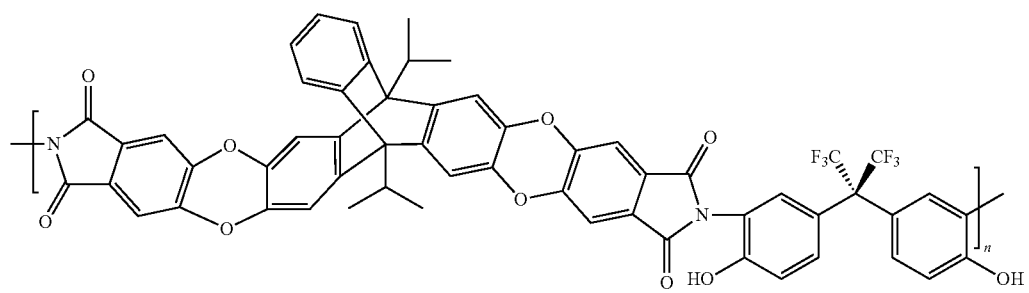

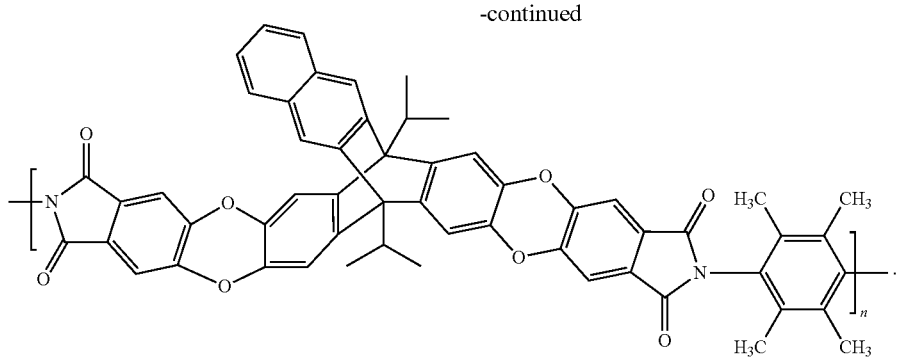

In an exemplary embodiment, the triptycene-based aromatic polyimide can be synthesized by reacting the triptycene-based monomer with a multi-amine. In an embodiment, the multi-amine can include a diamine, triamine, tetramine, and an amine having 5 or more amino groups.

An exemplary embodiment of a synthesis can include the reaction scheme shown below:

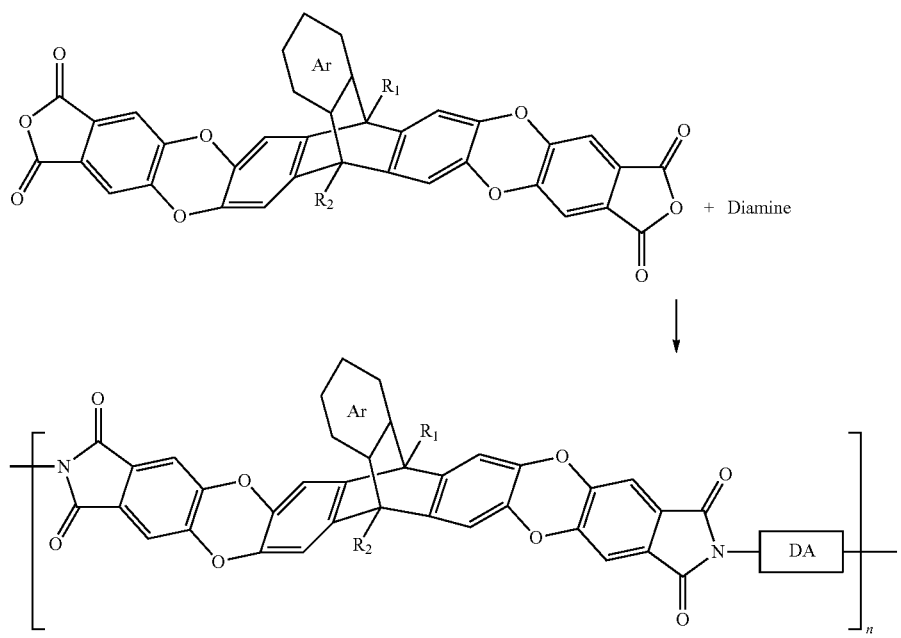

AR, R1, and R2 have the same meaning as described above. DA is a linking group derived from the diamine. In an embodiment, the diamine can include those described in Schemes 2 and 3. In an embodiment, DA can include AR', as described in Scheme 2.

In another embodiment, the triptycene-based aromatic polyimide can be synthesized by reacting the triptycene-based monomer with a triamine or multi-amine. In this embodiment, an insoluble microporous network of polyimides can be formed that can be used for gas storage (e.g., $H_2$, $CO_2$, $CH_4$, and the like). An exemplary reaction scheme is shown in Scheme 5.

In another embodiment, a polypyrrolone can by synthesized by reacting the triptycene-based monomer with a multi-amine. An exemplary reaction scheme is shown in Scheme 4.

As mentioned above, polyimides of the present disclosure can be used to form membranes that can be used in gas separation. The membranes including the polyimides can be formed using conventional techniques.

As mentioned above, the membranes of the present disclosure can be used in conventional gas separation systems such as systems to enrich a specific gas content in a gas mixture (e.g., oxygen enrichment, nitrogen enrichment, and the like). In addition, the membranes can be used in hydrogen gas separations.

In general, a first gas is separated from a first gas mixture with a membrane of the present disclosure to form a second gas mixture that is enriched in one or more components of the first gas mixture. In an embodiment, the result can be the separation of a gas(es) from another gas(es) such as in oxygen/nitrogen, hydrogen/methane, hydrogen/nitrogen, carbon dioxide/methane, carbon dioxide/nitrogen, hydrogen/$C_2$+ hydrocarbons, hydrogen sulfide/methane, carbon dioxide/hydrogen sulfide, ethylene/ethane, propylene/propane, water vapor/hydrocarbons, $C_2$+/hydrogen, $C_2$+/methane etc.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

See Attachment A

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

REFERENCES

1. Y. J. Cho, and H. B. Park, 'High Performance Polyimide with High Internal Free Volume Elements', Macromolecular Rapid Communications, 32 (2011), 579-586.
2. B. S. Ghanem, N. B. McKeown, P. M. Budd, N. M. Al-Harbi, D. Fritsch, K. Heinrich, L. Starannikova, A. Tokarev, and Y. Yampolskii, 'Synthesis, Characterization, and Gas Permeation Properties of a Novel Group of Polymers with Intrinsic Microporosity: Pim-Polyimides', Macromolecules, 42 (2009), 7881-7888.
3. P. M. Budd, K. J. sayib, C. E. Tattershall, B. S. Ghanem, K. J. Reynolds, N. B. McKeown, and D. Fritsch, 'Gas Separation Membranes from Polymers of Intrinsic Microporosity', Journal of Membrane Science, 251 (2005), 263-269.
4. S. Thomas, I. Pinnau, N. Y. Du, and M. D. Guiver, 'Pure- and Mixed-Gas Permeation Properties of a Microporous Spirobisindane-Based Ladder Polymer (PIM-1)', Journal of Membrane Science, 333 (2009), 125-131.
5. C. L. Staiger, S. J. Pas, A. J. Hill, and C. J. Cornelius, 'Gas Separation, Free Volume Distribution, and Physical Aging of a Highly Microporous Spirobisindane Polymer', Chemistry of Materials, 20 (2008), 2606-2608.
6. C. G. Bezzu, M. Carta, A. Tonkins, J. C. Jansen, P. Bernardo, F. Bazzarelli, and N. B. McKeown, 'A Spirobifluorene-Based Polymer of Intrinsic Microporosity with Improved Performance for Gas Separation', Advanced Materials, 24 (2012), 5930.
7. R. L. Burns, and W. J. Koros, 'Defining the Challenges for $C_3H_6/C_3H_8$ Separation Using Polymeric Membranes', Journal of Membrane Science, 21 1 (2003), 299-309.

Scheme (1): Synthetic Route to Novel Dianhydrides

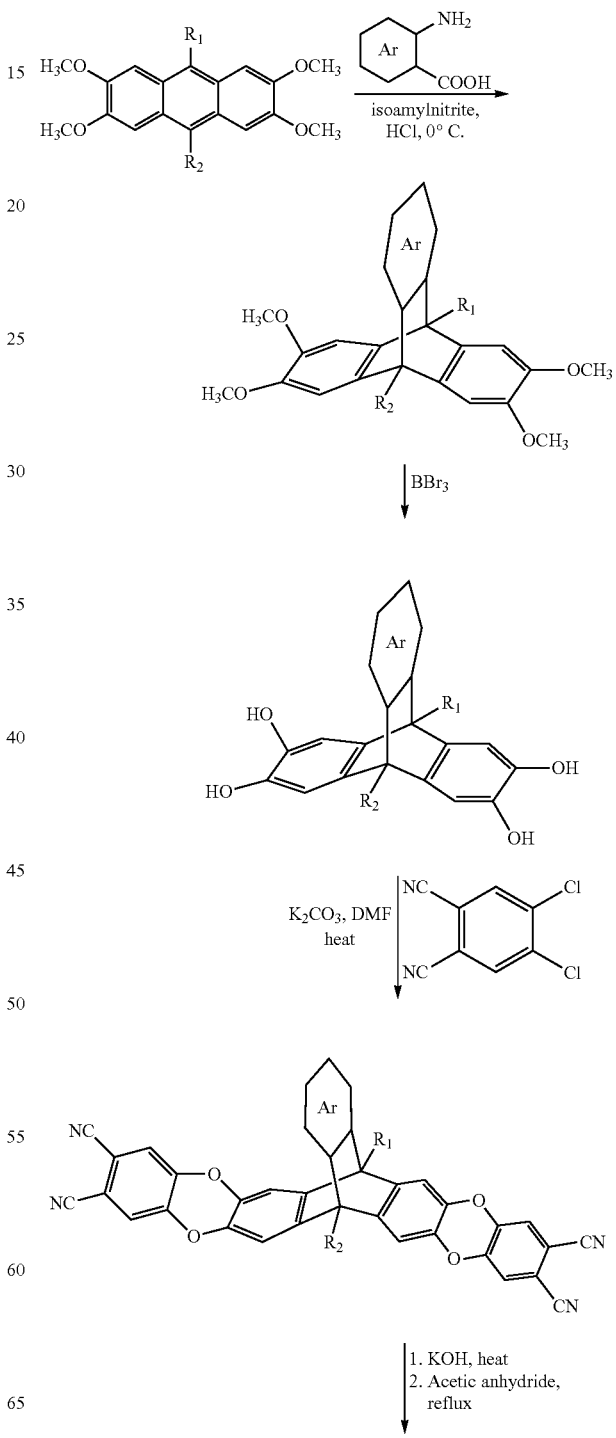

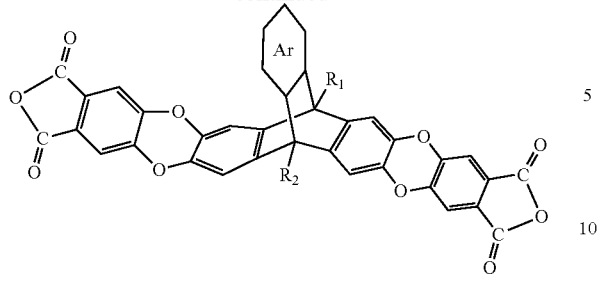
Where Ar is a substituted or non-substituted aromatic moiety and R, Ri and R$_2$ are branched alkyl groups or hydrogen.
Scheme (2): Synthetic Route to Novel Polyimides
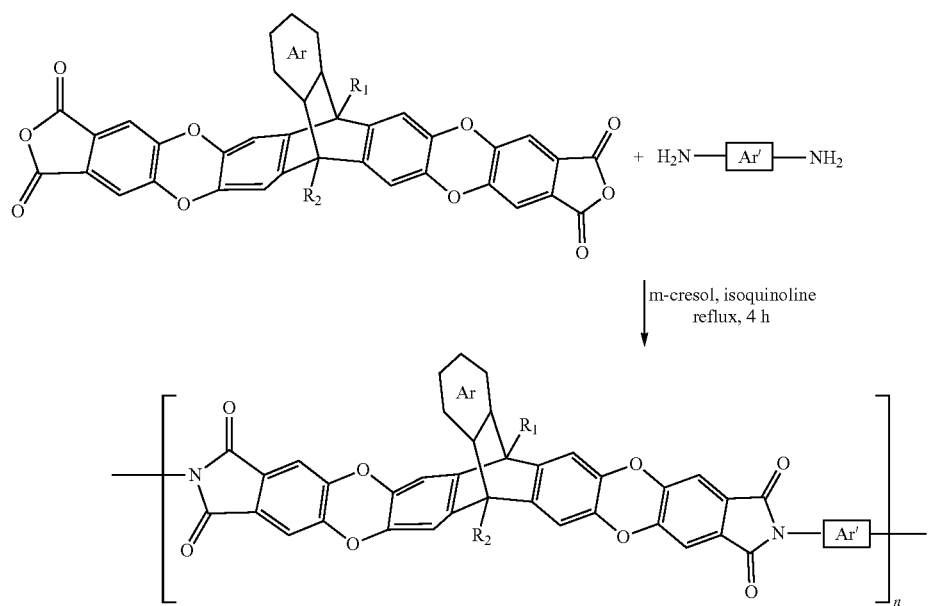
Specific examples of polyimides prepared from 9,10-diisoproply dianhydride.
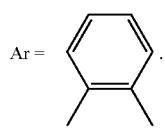
I
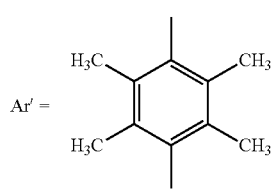
(1)
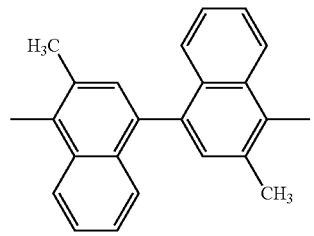
(2)
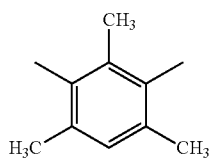
(3)
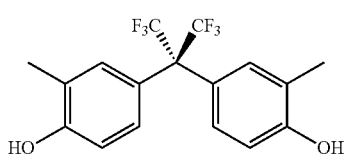
(4)

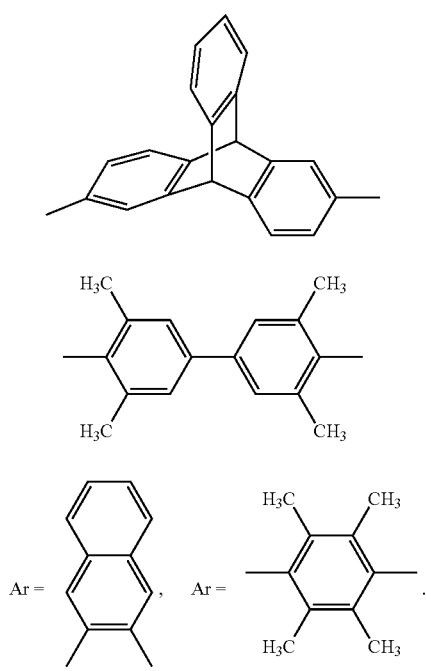
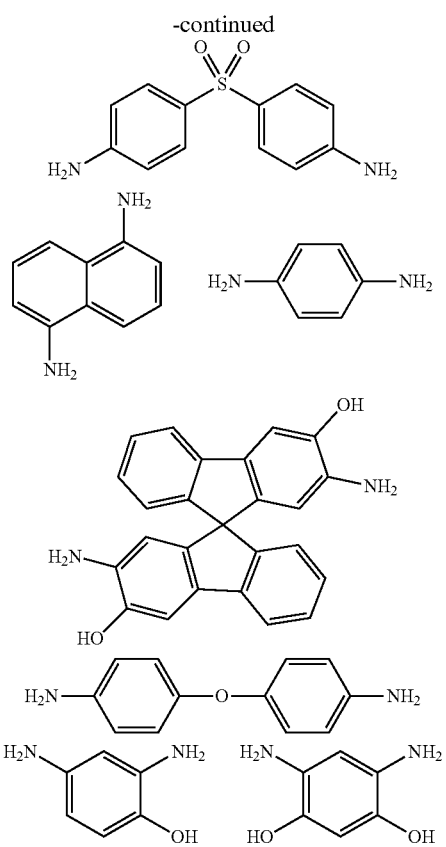

Scheme (3): Other Diamines for the Synthesis of Novel Polyimides

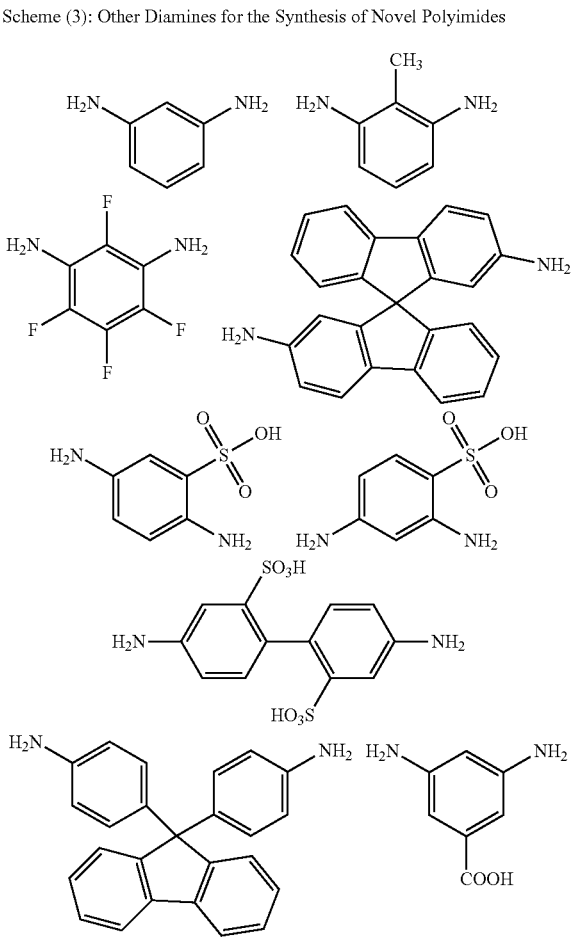

Other Potential Applications of the Prepared Polyimides

Due to their good solubilities, thermal and chemical stabilities, and high microporosities, these materials are potentially implementable in a wide range of important industrial applications related to thermally stable coatings, low dielectric constant films, optoelectronic materials, sensors and gas storage media.

Other Classes of Materials Derivable from these Novel Dianhydrides

Other interesting polymers which can also be prepared from these novel dianhydride monomers are polypyrrolones. These materials possess more rigidity than polyimides and thus can be more efficient molecular sieves. Polypyrrolones are generally prepared by the polycondensation reaction of a dianhydride monomer and a tetra-amine monomer as displayed in the following scheme:

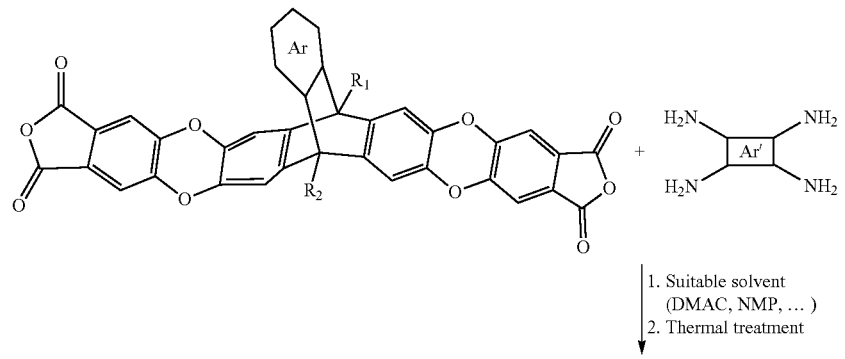
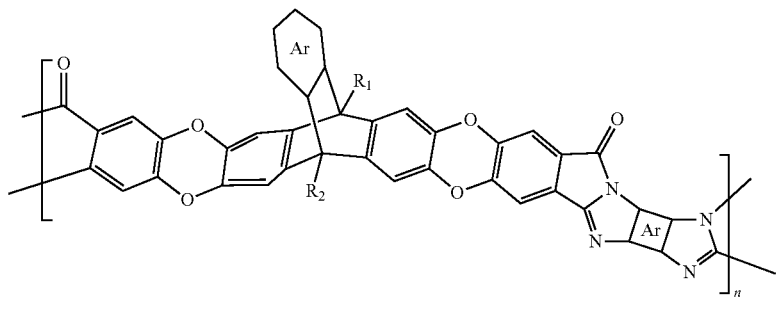
Polypyrrolone
The dianhydrides can also react with triamine or multi-amines to produce insoluble microporous network polyimides for other applications, such as $H_2$, $CO_2$ and $CH_4$ storage, as shown below.
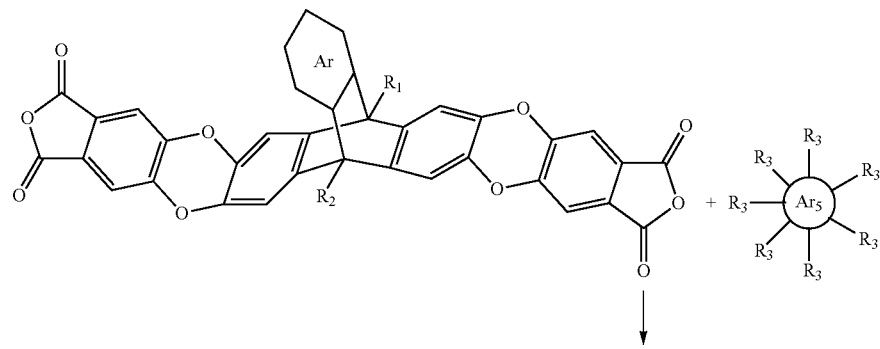

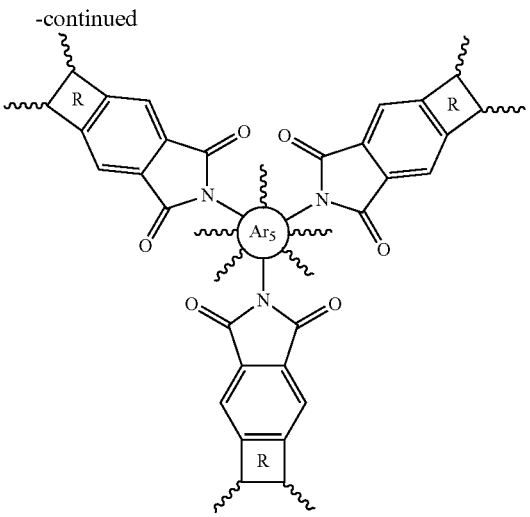

Gas Transport Testing Method

The gas permeability of the membranes was determined using the constant-volume/variable-pressure method. The membranes were degassed in the permeation test apparatus on both sides under high vacuum at 35° C. for at least 24 h. The increase in permeate pressure with time was measured by a MKS Baratron transducer (range from 0 to 10 torr). The permeability of all gases was measured at 2 bar and 35° C. and was calculated by $$P = 10^{10} \frac{V_d l}{p_{up} TRA} \frac{dp}{dt}$$

where P is the permeability (Barrers) (1 Barrer=$10^{-10}$ cm$^3$ (STP) cm/(cm$^2$ s cmHg)), $p_{up}$ is the upstream pressure (cmHg), dp/dt is the steady-state permeate-side pressure increase (cmHg/s), $V_d$ is the calibrated permeate volume (cm$^3$), l is the membrane thickness (cm), A is the effective membrane area (cm$^2$), T is the operating temperature (K), and R is the gas constant (0.278 cm$^3$ cmHg/(cm$^3$ (STP) K)). The pure-gas selectivity of gas A over gas B was calculated by the ratio of their permeabilities $$\alpha_B^A = P_A/P_B$$

Tabulation of Data on Permeability/Selectivity Trade-off Figures $O_2/N_2$

| Polymer | Permeability $O_2$ (Barrer) | α ($O_2/N_2$) | Reference |
|---|---|---|---|
| 6FDA-DATRI | 39 | 4.8 | [1] |
| PIM-PI-1 | 150 | 3.2 | [2] |
| PIM-PI-2 | 39 | 4.3 | |
| PIM-PI-3 | 85 | 3.7 | |
| PIM-PI-4 | 64 | 4.0 | |
| PIM-PI-7 | 77 | 4.1 | |
| PIM-PI-8 | 545 | 3.4 | |
| PIM-7 | 190 | 4.5 | [3] |
| PIM-1(a) | 1300 | 3.8 | [4] |
| PIM-1(b) | 786 | 3.3 | [5] |
| PIM-SBF | 2640 | 3.4 | [6] |
| TPDA-1 | 660 | 6.2 | [This work] |

Tabulation of Data on Permeability/Selectivity Trade-off Figures $H_2/N_2$

| Polymer | Permeability $H_2$ (Barrer) | α ($H_2/N_2$) | Reference |
|---|---|---|---|
| 6FDA-DATRI | 257 | 32.0 | [1] |
| PIM-PI-1 | 530 | 11.3 | [2] |
| PIM-PI-2 | 220 | 24.4 | |
| PIM-PI-3 | 360 | 15.7 | |
| PIM-PI-4 | 300 | 18.8 | |
| PIM-PI-7 | 350 | 18.4 | |
| PIM-PI-8 | 1600 | 10.0 | |
| PIM-7 | 860 | 20.5 | [3] |
| PIM-1(a) | 3600 | 11.0 | [4] |
| PIM-1(b) | 2332 | 9.8 | [5] |
| PIM-SBF | 6320 | 8.1 | [6] |
| TPDA-1 | 4415 | 42 | [This work] |

$Co_2/CH_4$

| Polymer | Permeability $Co_2$ (Barrer) | α ($Co_2/CH_4$) | Reference |
|---|---|---|---|
| 6FDA-DATRI | 189 | 30.5 | [1] |
| PIM-PI-1 | 1100 | 14.3 | [2] |
| PIM-PI-2 | 210 | 23.3 | |
| PIM-PI-3 | 520 | 19.3 | |
| PIM-PI-4 | 420 | 21.0 | |
| PIM-PI-7 | 510 | 18.9 | |
| PIM-PI-8 | 3700 | 14.2 | |
| PIM-7 | 1100 | 17.7 | [3] |
| PIM-1(a) | 6500 | 15.0 | [4] |
| [6] | 12.6 | 13900 | PIM-SBF |
| [This work] | 22.0 | 2450 | TPDA-1 |

$C_3H_6/C_3H_8$

| Reference | α ($C_3H_6/C_3H_8$) | Permeability $C_3H_6$ (Barrer) | Polymer |
|---|---|---|---|
| [7] | 16 | 0.1 | Matrimid ® (a) |
| | 4 | 0.003 | Matrimid ®-Thermid 85/15 |
| | 21 | 0.09 | Pyralin 2566 |
| | 4.3 | 9.0 | PPO |
| | 3.3 | 52 | EC |
| | 2.6 | 15.2 | CA |
| | 1.4 | 25 | PSF |
| | 10 | 0.13 | 6FDA-mPD |
| | 15 | 0.58 | 6FDA-IpDA |

-continued

| | | |
|---|---|---|
| 16 | 0.89 | 6FDA-6FpDA |
| 10 | 0.1 | Matrimid ® (b) |
| 13 | 0.15 | 6FDA-33'DMDB |
| 8.6 | 37 | 6FDA-TeMPD |
| 11 | 30 | 6FDA-TrMPD |
| 20 | 1.8 | 6FDA-DOBT |
| 13 | 3.2 | 6FDA-TeMPD |
| 9.1 | 2.3 | PPO |
| 2.0 | 54 | P4MP |
| 1.7 | 260 | 1.2PB |
| 11 | 0.48 | 6FDA-ODA |
| [4] 2.5 | 8750 | PIM-1 |
| [This work] 15 | 800 | TPDA-1 |

Following is a tabulation of gas transport properties for the prepared polyimides specified in Scheme (2). The polymer naming is as such: TPDA-#, where TPDA refers to the 9,10-diisopropyl dianhydride, and # refers to the diamine used as per the numbering shown in Scheme (2).

Structurally Related Novel Polyimides

| TPDA-6 | TPDA-5 | TPDA-4 | TPDA-3 | TPDA-2 | TPDA-1 | |
|---|---|---|---|---|---|---|
| Permeability Barrer: 1 Barrer = $10^{-10}$ cm$^3$ (STP) cm s$^{-1}$ cm$^{-2}$ cm Hg$^{-1}$) | | | | | | Gas |
| 1026 | 646 | 138 | 2097 | 725 | 1917 | He |
| 2368 | 1466 | 178 | 4563 | 1737 | 4415 | $H_2$ |
| 98 | 71 | 4.0 | 161 | 108 | 106 | $N_2$ |
| 486 | 318 | 19.9 | 814 | 446 | 660 | $O_2$ |
| 101 | 64 | 2.6 | 161 | 125 | 111 | $CH_4$ |
| 2050 | 1406 | 98 | 3140 | 2272 | 2450 | $CO_2$ |
| Ideal Selectivity | | | | | | Gas Pair |
| 5.0 | 4.5 | 5.0 | 5.1 | 4.1 | 6.2 | $O_2/N_2$ |
| 24 | 21 | 45 | 28 | 16 | 42 | $H_2/N_2$ |
| 20 | 17 | 38 | 20 | 18 | 22 | $CO_2/CH_4$ |

All data was collected at 2 bar feed pressure and 35° C. using the constant-volume/variable-pressure technique.

We claim at least the following:

1. A composition, comprising:
a triptycene-based aromatic polyimide having the following structure:

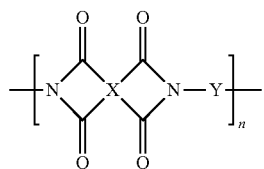

wherein n is 1 to 10,000 wherein X is:

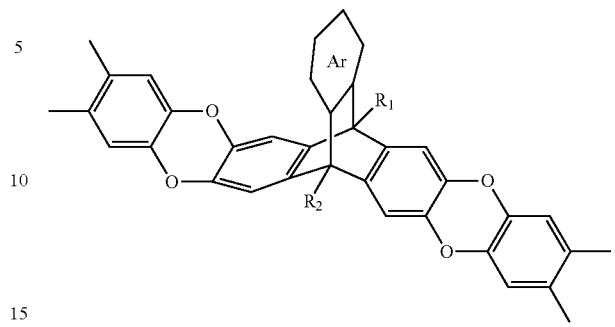

wherein Y is a divalent organic group, wherein AR is a substituted or un-substituted aromatic moiety, wherein R1 is a substituted or un-substituted branched alkyl group, wherein R2 is hydrogen, a substituted or un-substituted alkyl group, substituted or un-substituted branched alkyl group, or substituted or un-substituted phenyl group.

2. The composition of claim 1, wherein the divalent organic group is selected from the group consisting of: aromatic diamine, aromatic triamine, and aromatic tetramine.

3. The composition of claim 1, wherein the substituted or un-substituted aromatic moiety is selected from the group consisting of: phenyl and naphthyl.

4. The composition of claim 1, wherein substituted or un-substituted R1 and R2 are independently is selected from the group consisting of: substituted or un-substituted branched C3 to C5 alkyl groups.

5. The composition of claim 1, wherein AR is

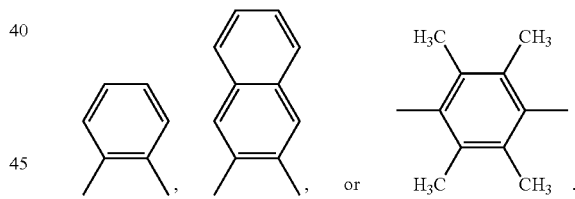

6. The composition of claim 1, wherein Y is AR', and AR' is

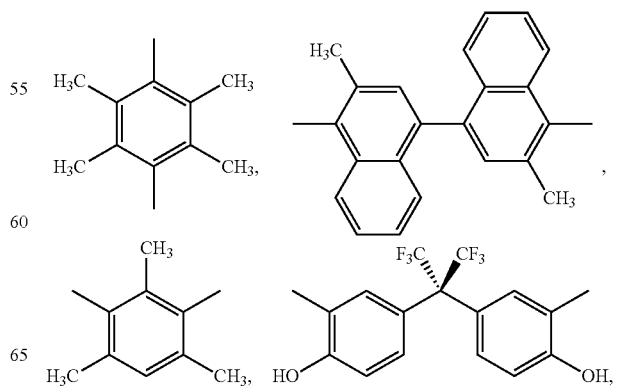

-continued

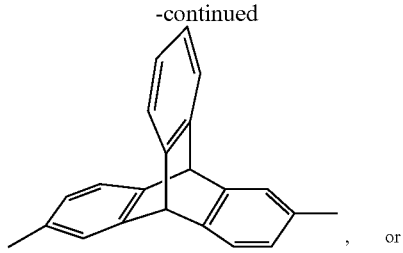

, or

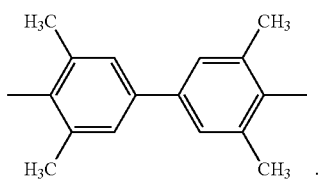

7. A composition, comprising a monomer as shown in the following structure:

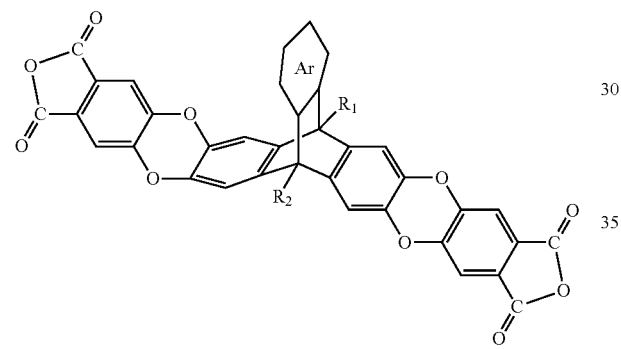

wherein AR is a substituted or un-substituted aromatic moiety, wherein R1 is hydrogen or a substituted or un-substituted branched alkyl group, and wherein R2 is hydrogen, or a substituted or un-substituted alkyl group, substituted or un-substituted branched alkyl group, or substituted or un-substituted phenyl group.

8. The composition of claim 7, wherein AR is

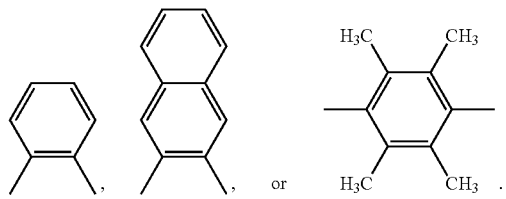

9. The composition of claim 7, wherein the substituted or un-substituted aromatic moiety is selected from the group consisting of: phenyl and naphthyl.

10. The composition of claim 7, wherein substituted or un-substituted R1 and R2 are independently is selected from the group consisting of: substituted or un-substituted branched C3 to C5 alkyl groups.

11. A method of making a dianhydride, comprising:

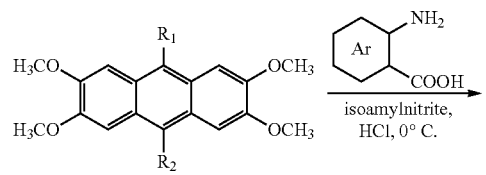

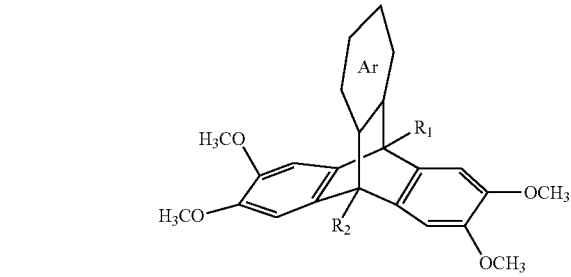

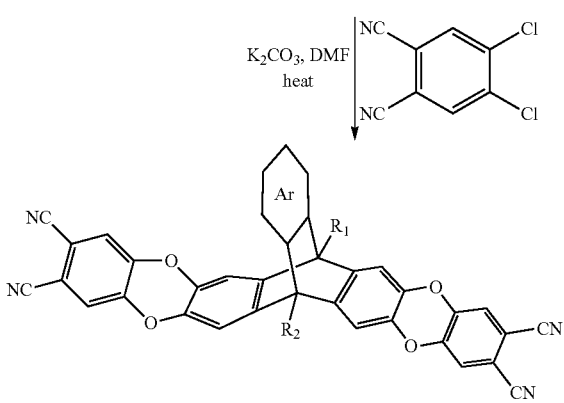

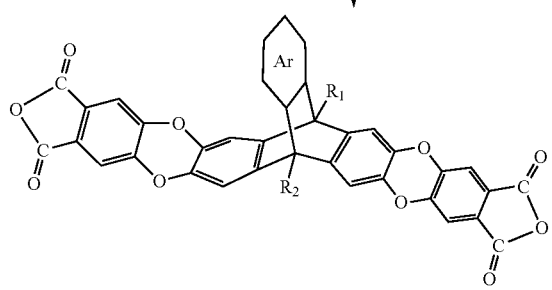

wherein AR is a substituted or un-substituted aromatic moiety, wherein R1, R2, and R are each independently selected from: wherein R1 is substituted or un-substituted branched alkyl group, and wherein R2 is hydrogen, a substituted or un-substituted alkyl group, substituted or un-substituted branched alkyl group, or substituted or un-substituted phenyl group.

12. The composition of claim 11, wherein AR is

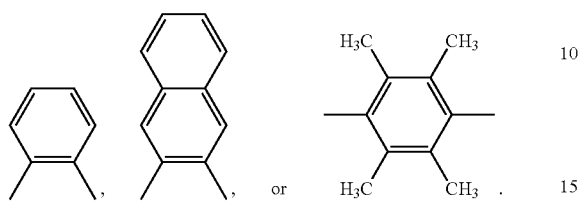

13. The composition of claim 11, wherein the substituted or un-substituted aromatic moiety is selected from the group consisting of: phenyl and naphthyl.

14. The composition of claim 1, wherein substituted or un-substituted R, R1, and R2 are each independently is selected from the group consisting of: substituted or un-substituted branched C3 to C5 alkyl groups.

15. A method for making a polyimide, comprising: reacting a monomer of claim 7 with a multi-amine to form a polyimide.

16. The method of claim 15, wherein the multi-amine is selected from the group consisting of a diamine, triamine, tetramine, and an amine having 5 or more amino groups.

17. The method of claim 15, wherein the reaction scheme is as follows:

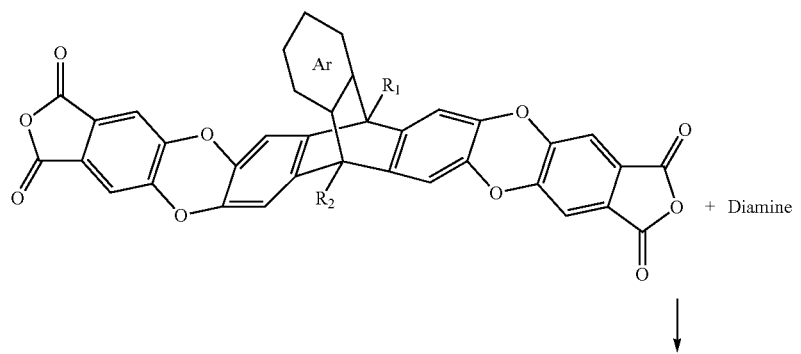

wherein AR is a substituted or un-substituted aromatic moiety, wherein R1 is substituted or un-substituted branched alkyi group, and R2 is hydrogen, a substituted or un-substituted alkyi group, substituted or un-substituted branched alkyi group, or substituted or un-substituted phenyl group, and DA is a linking group derived from the diamine.

18. The method of claim 17, wherein the diamine includes

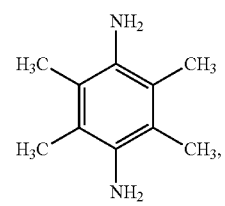

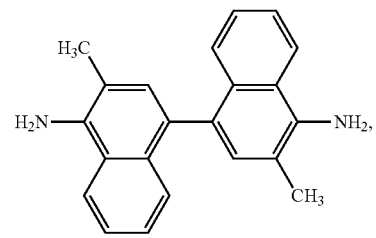

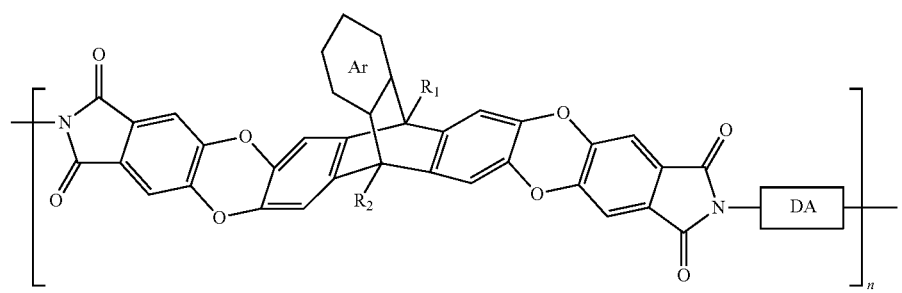

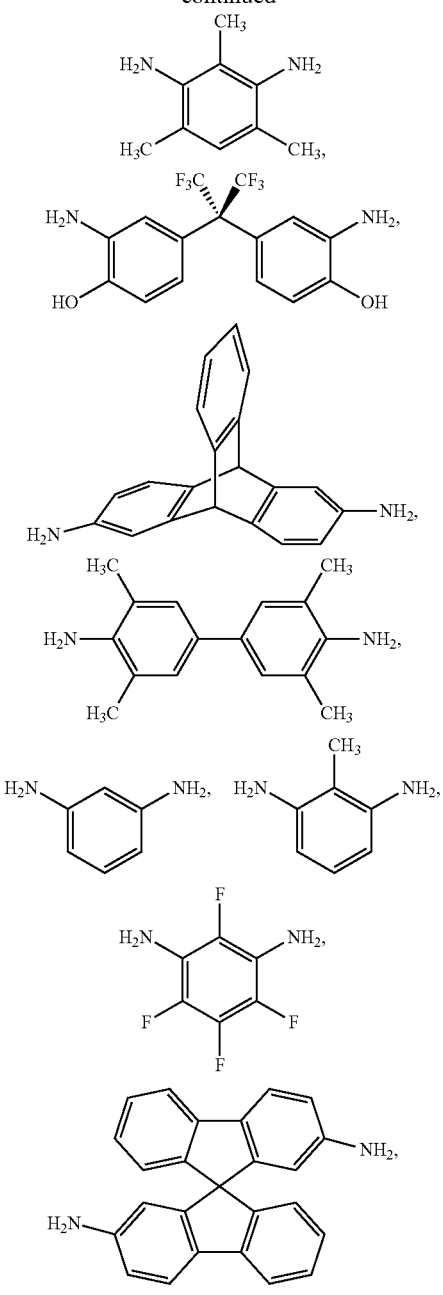
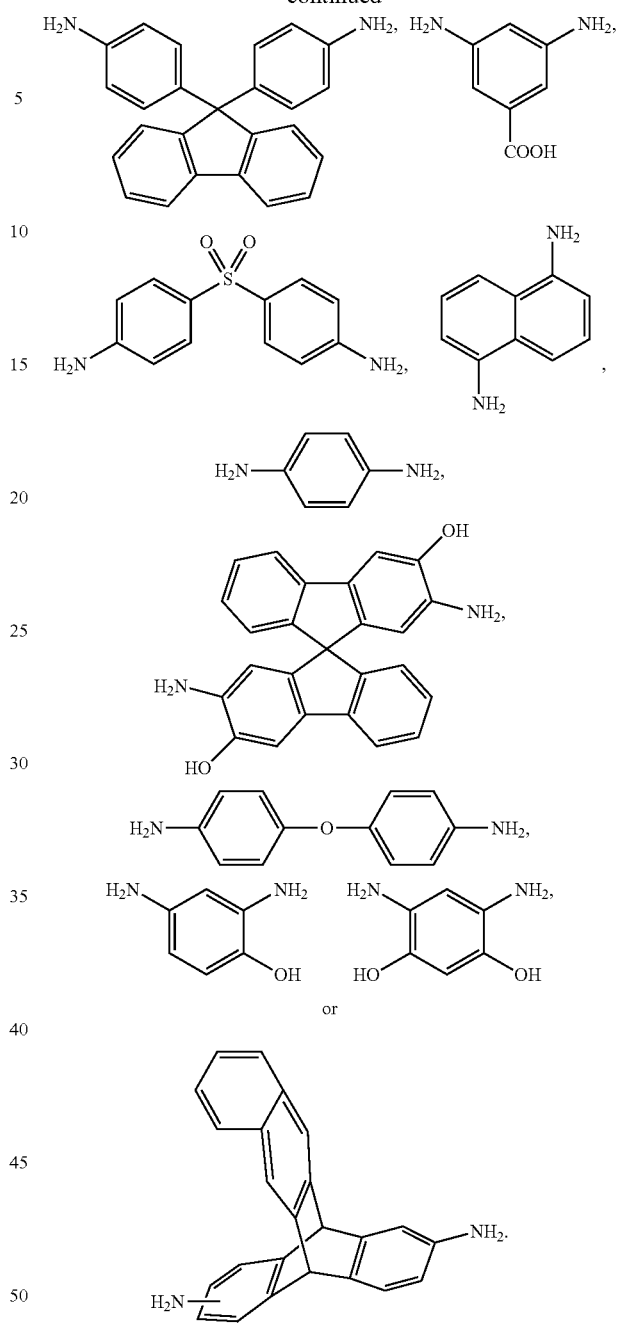
19. The method of claim 18, wherein the DA is derived from one of
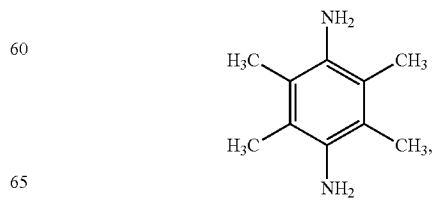

-continued
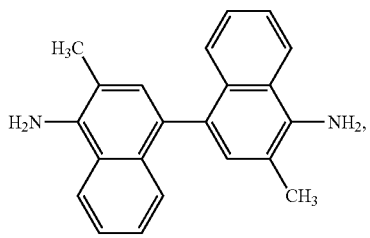
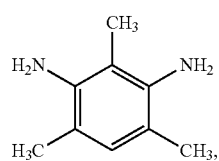
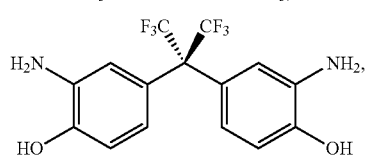
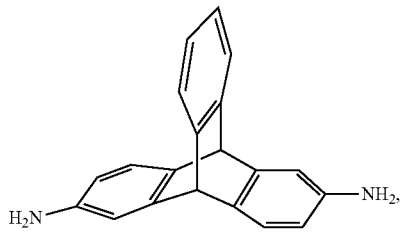
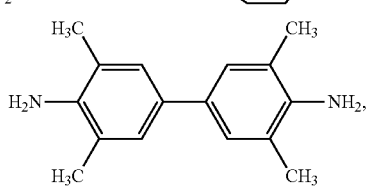
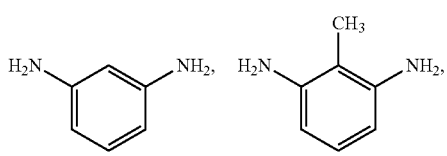
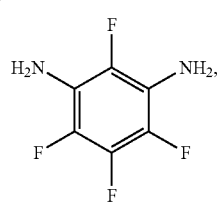
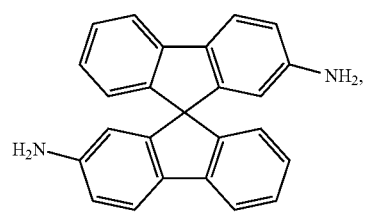
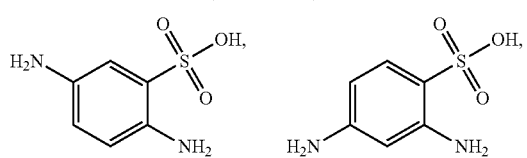
-continued
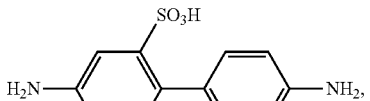
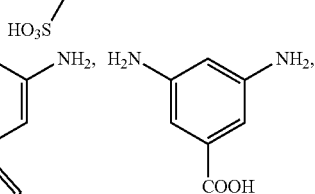
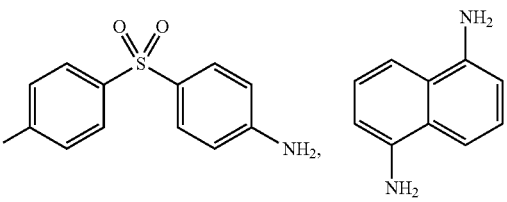
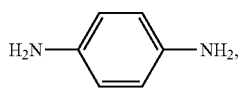
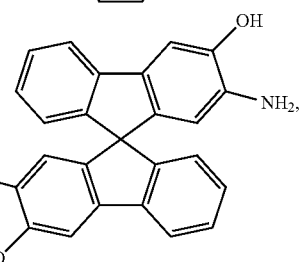
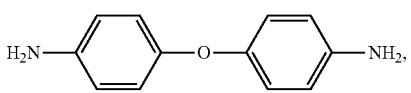
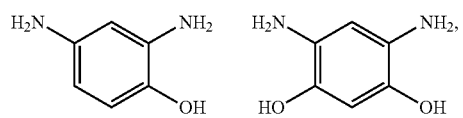
or
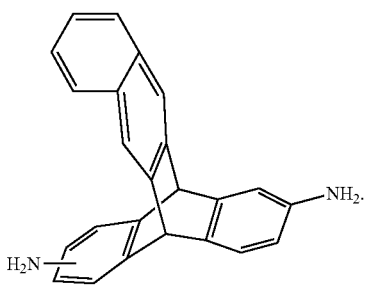
20. A method for making a polyimide, comprising: reacting a monomer of claim 7 with a multi-amine to form a polypyrrolone.

21. The method of claim 20, wherein the reaction scheme is as follows:

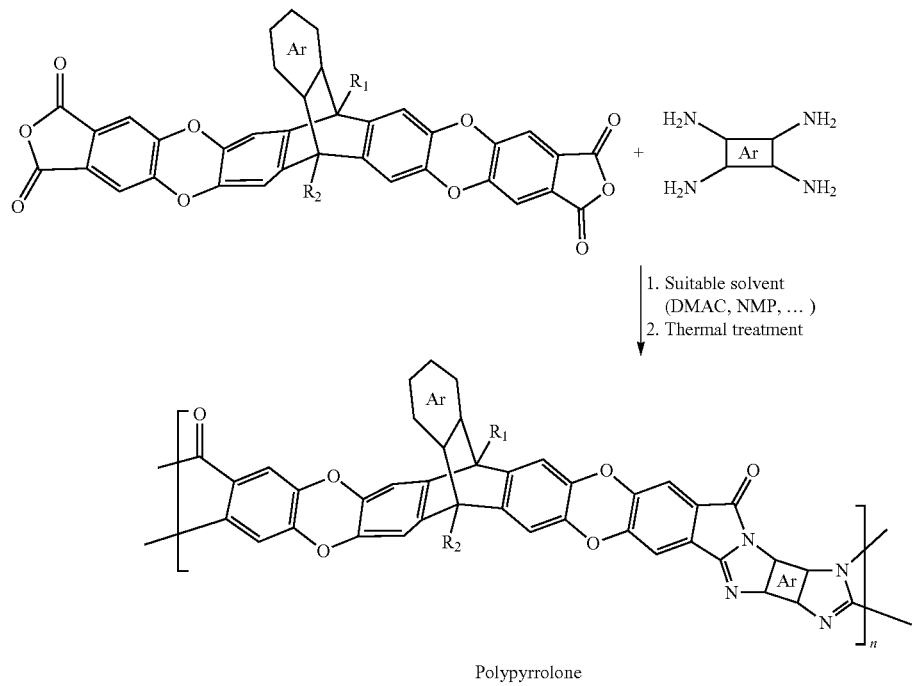

wherein each AR is independently selected.

22. A membrane, comprising: a polyimide of claim 1.

23. A method of separating a gas from a gas mixture, comprising: separating a first gas from a first gas mixture with a membrane of claim 22 to form a second gas mixture.

24. The method of claim 23, wherein the first gas is selected from the group consisting of: He, $H_2$, $CO_2$, $H_2S$, $O_2$, $N_2$, $CH_4$, saturated $C_2+$ hydrocarbons, $C_2H_4$, $C_2H_6$, $C_3H_6$, $C_3H_8$ and a combination thereof.

25. The method of claim 23, wherein the second gas mixture is oxygen enriched when compared to the first gas mixture.

26. The method of claim 23, wherein the second gas mixture is nitrogen enriched when compared to the first gas mixture.

* * * * *